United States Patent [19]
Sokolow et al.

[11] Patent Number: 5,522,903
[45] Date of Patent: Jun. 4, 1996

[54] FINGER PROSTHESIS

[75] Inventors: Constantin Sokolow, Paris; Christian Bour, Lemans; Yves Bouchon, Nancy; Hervé Dinville, Saint-Parres-aux-Tertres, all of France

[73] Assignee: JBS S.A., Troyes, France

[21] Appl. No.: 339,242

[22] Filed: Nov. 10, 1994

[30] Foreign Application Priority Data

Nov. 10, 1993 [FR] France .................................. 93 13414

[51] Int. Cl.⁶ ...................................................... A61F 2/42
[52] U.S. Cl. .................................................. 623/21; 623/18
[58] Field of Search ............................... 623/16, 18, 19, 623/20, 21

[56] References Cited

U.S. PATENT DOCUMENTS

| | | |
|---|---|---|
| 3,869,729 | 3/1975 | Attenborough . |
| 4,106,128 | 8/1978 | Greenwald et al. ............... 623/21 |
| 4,304,011 | 12/1981 | Whelan, III ....................... 623/21 |
| 5,147,386 | 9/1992 | Carignan et al. . |

FOREIGN PATENT DOCUMENTS

| | | |
|---|---|---|
| 0278184 | 8/1988 | European Pat. Off. . |
| 2237613 | 2/1975 | France . |
| 7634751 | 5/1977 | Germany . |
| 2045085 | 10/1980 | United Kingdom . |

*Primary Examiner*—David Isabella
*Attorney, Agent, or Firm*—Spencer & Frank

[57] ABSTRACT

A finger prosthesis includes a first screw to be received in an intramedullary canal of a phalange. The first screw includes a first head defining a first longitudinal bore therein. There is provided a second screw to be received in an intramedullary canal of another, adjoining phalange. The second screw includes a second head defining a second longitudinal bore therein. The prosthesis further has a first joint part having a convex semi-cylindrical surface, a transverse slot and a bore hole, a pivot pin held in the bore hole and traversing the transverse slot. The first piston is secured to the pivot pin for swinging motion in the transverse slot. The first piston is received in the first longitudinal bore for sliding motions therein. There is further provided a second joint part situated between the first head and the first joint part and having a concave semi-cylindrical surface slidingly contacting the convex semi-cylindrical surface of the first joint part. A second piston extends from the first joint part and is slidingly received in the second longitudinal bore. An arrangement prevents the first and second pistons from angular displacements relative to the respective first and second screws.

5 Claims, 1 Drawing Sheet

FINGER PROSTHESIS

BACKGROUND OF THE INVENTION

The present invention relates to a finger prosthesis with double piston for pivotal and sliding movement.

It is a well-known practice to substitute a finger joint damaged by rheumatism by surgical implantation of an artificial joint i.e. prosthesis which allows recovery of the patient and practical use of the damaged finger.

However, it is rather difficult to implant the prostheses applied nowadays and they allow only a limited angular motion of the phalanges with respect to the original one.

The known artificial joints generally consist of two parts connected by a joint and are fixed in the bones by osteointegration or by the use of bone cement. These prostheses are generally loosening, luxating or are damage in short time due to the loading.

SUMMARY OF THE INVENTION

It is the object of the present invention to offer means for avoiding the above inconveniences. This invention, as it is characterized solves the problem of providing an improved finger prosthesis which allows a free motion of the phalanges and keeps one part of the joint perfectly safe against rotation with respect to the other part in order to avoid the risk of accidental unscrewing thereof.

The finger prosthesis comprises a joint for pivotal movement between two bones, including intramedullary stems adapted to be secured in the intramedullary canals of the two bones after resection. The prosthesis is essentially characterized in that the joint includes a convex semi-cylindrical part and a concave semi-cylindrical part in the form of a cushion having the same radius of curvature as the convex part has and rotating on the surface of the convex part, and that the stems connecting the joint and the bones are pistons slidably received in longitudinal bores provided in the hollow heads of self-cutting screws secured in the bones.

According to a non limiting embodiment of the invention, the convex part of the joint is provided with a central transverse slot and a bore receiving a pin being the axis of rotation of the piston bearing the concave part in form of a cushion which in turn is supported by the hollow head of the corresponding self-cutting screw.

The connection between a stem and a self-cutting screw may contain at least one flat part in order to prevent rotation.

The central transverse slot in the convex part has a back wall which contains the geometrical axis of the other stem and a bottom wall forming an angle of about 60° with said axis.

The bore in the convex part receiving the pin is arranged in a way that the distance between said bore and the bottom wall as well as the distance between said bore and the geometrical axis of the other piston is greater then the radius of the piston. The saw-tooth section of the thread of the self-cutting screws is arranged inversely with respect to the conventional orientation.

The advantages of the present invention are essentially that the prosthesis is fixed firmly in the bones and at the same time enables certain longitudinal movement in accordance with the pivotal movement of the phalanges even in the extreme positions and in this way allows a free and natural movement thereof.

DESCRIPTION OF THE PREFERRED EMBODIMENT

Figure 1:
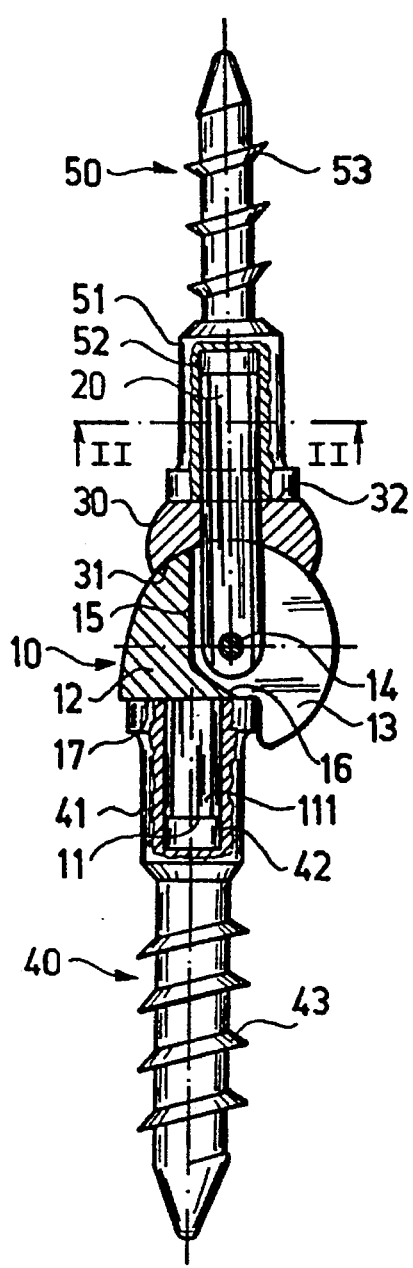
FIG. 1 is a side elevational view of the prosthesis, partly in section.
Figure 3:
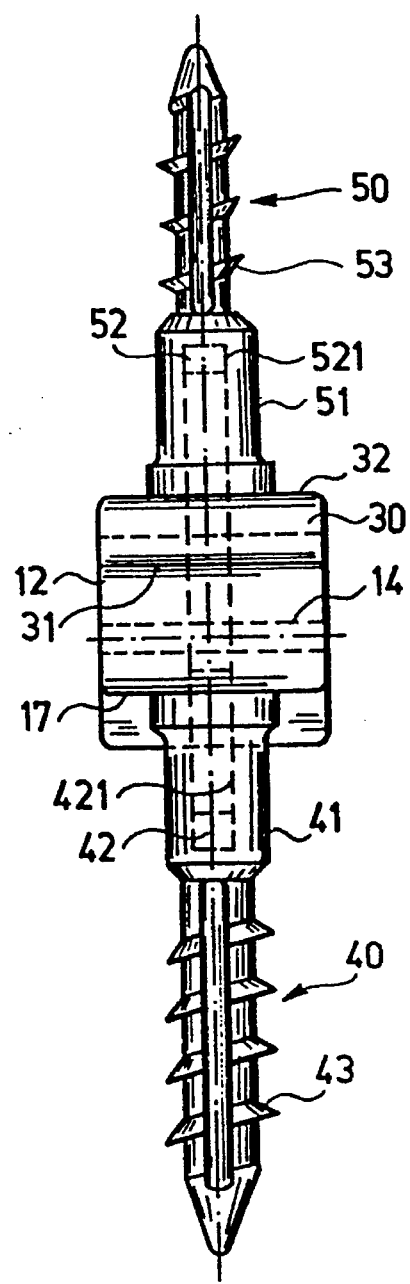
FIG. 3 is a front view of the prosthesis according to the invention.
Figure 2:
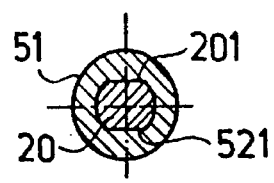
FIG. 2 is a sectional view taken along line II—II of FIG. 1.

The prosthesis shown FIGS. 1–3 comprises a joint 10 fixed in the free ends of the phalanges by pistons 11 and 20 received in the holes 42, 52 of the hollow head 41, 51 of respective self-cutting screws 40 and 50, wherein a parallelogram based cushion 30 with a semi-cylindrical concave surface 31 is connected to a second semi-cylindrical part 12 provided with a convex surface.

The joint 10 includes the semi-cylindrical convex part (first joint part) 12 provided with a central transverse slot 13. This part contains a bore receiving a pin 14 as the axis of rotation of piston 20. The cushion 30 (concave semi-cylindrical part or second joint part) is provided with a semi-cylindrical concave surface 31 of the same radius as the convex semi-cylindric surface 12 of the other part which is supported by the first one in order to provide a pivot and a plane on its external surface 32 which in turn is supported by the head of the corresponding screw.

It is to be noted that pistons 11, 20 and self-cutting screws 40, 50 are connected to each other in a way which prevents rotation between the elements by flattenings (flat parts) 111 and 201 provided on the outer surfaces of the pistons 11 and 20 and by similar flat parts 421, 521 provided in the holes 42, 52 within the hollow heads 41, 51 of screws 40 and 50. The flat parts prevent accidental unscrewing of one or the other screw.

The central transverse slot 13 in semi-cylindrical convex part 12 has a back wall 15 the plane of which includes the geometrical axis of piston 11 connected to said semi-cylindrical convex part 12 and a bottom wall 16 which forms an angle of about 60° with the same axis.

The distance between the pin 14 of the piston 20 and the base 17 of semi-cylindrical convex part 12 is greater than the radius of the pistons 11 and 20.

Accordingly, it is sufficient to screw self-cutting screws 40 and 50 in the medullary canals of both bones after carrying out the necessary resection of the bones. Then, piston 11 of the joint 10 is introduced in the hole 42 of screw 40 and piston 20 together with cushion 30 is introduced in the hole 52 of screw 50 to establish the artificial joint between the phalanges.

The pivotal movement of the phalanges is limited by wall 15, along the geometrical axis of piston 11, meanwhile there is a free pivotal movement in the other direction, where the transverse bottom wall 16 is arranged.

Preferably the cross-section of threads 43 of 53 self-cutting screws 40 and 50 of a saw-tooth shape is arranged inversely with respect to the conventional orientation in order to obtain the maximum resistance to external axial loads on the hollow heads 41, 51. The screws may be of cylindrical or at least partially conical shape.

Undesired stresses and loosening of the joint due to such stresses may be avoided within the system according to the invention.

The sliding surfaces are preferably treated in order to improve service life and the coefficient of friction.

Due to the flat parts or hexagonal cross sections the pistons prevent accidental unscrewing of the screws.

What is claimed is:

1. A finger prosthesis comprising
   (a) a first screw to be received in an intramedullary canal of a phalange; said first screw including a first head defining a first longitudinal bore therein;
   (b) a second screw to be received in an intramedullary canal of a phalange; said second screw including a second head defining a second longitudinal bore therein;
   (c) a first joint part having a convex semicylindrical surface, a transverse slot and a bore hole;
   (d) a pivot pin held in said bore hole and traversing said transverse slot;
   (e) a first piston having an end secured to said pivot pin; said first piston being situated in said transverse slot for swinging motion in said transverse slot; said first piston being received in said first longitudinal bore for sliding motions therein;
   (f) a second joint part situated between said first head and said first joint part and having a concave semi-cylindrical surface slidingly contacting said convex semi-cylindrical surface of said first joint part;
   (g) a second piston contacting and extending from said first joint part and being received in said second longitudinal bore for sliding motions therein; and
   (h) rotation preventing means for preventing an angular displacement of the first and second pistons relative to respective said first and second screws.

2. The finger prosthesis as defined in claim 1, wherein said rotation preventing means comprises complemental flattened portions of said first and second pistons and said first and second longitudinal bores.

3. The finger prosthesis as defined in claim 1, wherein said second piston has a geometrical axis and said transverse slot has a back wall and a bottom wall forming part of said first joint part; said back wall containing said geometrical axis and said back wall forming an angle of about 60° with said geometrical axis.

4. The finger prosthesis as defined in claim 1, wherein said first joint part has a bottom wall and said second piston has a geometrical axis; said second piston extending from said bottom wall; further wherein a distance between said bore hole of said first joint part and said bottom wall of said first joint part and a distance between said bore hole of said first joint part and said geometrical axis is greater that a radius of said second piston.

5. The finger prosthesis as defined in claim 1, wherein at least one of said first and second screws has an inversely oriented self-cutting thread.

* * * * *